(12) United States Patent
Woodard

(10) Patent No.: US 12,274,431 B2
(45) Date of Patent: Apr. 15, 2025

(54) SURGICAL DISTRACTOR AND METHODS OF MANUFACTURE AND USE

(71) Applicant: WRIGHT MEDICAL TECHNOLOGY, INC., Memphis, TN (US)

(72) Inventor: Joseph Ryan Woodard, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 247 days.

(21) Appl. No.: 17/809,662

(22) Filed: Jun. 29, 2022

(65) Prior Publication Data

US 2023/0048763 A1 Feb. 16, 2023

Related U.S. Application Data

(60) Provisional application No. 63/232,305, filed on Aug. 12, 2021.

(51) Int. Cl.
  *A61B 17/02* (2006.01)
  *A61B 17/28* (2006.01)
  *A61B 17/60* (2006.01)

(52) U.S. Cl.
  CPC ........ *A61B 17/025* (2013.01); *A61B 17/0206* (2013.01); *A61B 17/2804* (2013.01); *A61B 17/60* (2013.01)

(58) Field of Classification Search
  CPC ... A61B 17/02; A61B 17/025; A61B 17/0206; A61B 17/28; A61B 17/2804; A61B 17/60
  See application file for complete search history.

(56) References Cited

U.S. PATENT DOCUMENTS

| | | | |
|---|---|---|---|
| 3,564,694 | A | 2/1971 | Millheiser |
| 4,896,661 | A | 1/1990 | Bogert et al. |
| 6,551,316 | B1 | 4/2003 | Rinner et al. |
| 2006/0155295 | A1 | 7/2006 | Supper et al. |

(Continued)

OTHER PUBLICATIONS

"MICA Minimally Invasive Foot Surgery, Chevron Osteotomy Surgical Technique," Wright Medical Technology, Inc., Oct. 17, 2017, 17 pages.

(Continued)

*Primary Examiner* — Christopher J Beccia
(74) *Attorney, Agent, or Firm* — DUANE MORRIS LLP

(57) ABSTRACT

Surgical instruments, such as distractors and methods of manufacture are provided for maintaining a displacement of bone determined to be necessary by a surgeon. For instance, a surgical distractor may include a first holder section, a second holder section, a first displacement element, a second displacement element, a positioning element, and a rotatable component having an opening. The second holder section may be coupled to the first holder section using one or more coupling elements coupled to both the first holder section and the second holder section. The first displacement element and the positioning element may be positioned on the first holder section and the second displacement element and the rotatable opening may be positioned on the second holder section configured to engage the first displacement element.

14 Claims, 12 Drawing Sheets

(56) References Cited

U.S. PATENT DOCUMENTS

| | | | |
|---|---|---|---|
| 2009/0088764 A1* | 4/2009 | Stad .................. | A61B 17/7086 606/151 |
| 2014/0031828 A1* | 1/2014 | Patel .................. | A61B 17/7077 606/90 |
| 2015/0313640 A1* | 11/2015 | O'Daly .................. | A61B 17/17 606/86 R |
| 2017/0113330 A1 | 4/2017 | Williams et al. | |
| 2020/0405359 A1 | 12/2020 | Hayes | |

OTHER PUBLICATIONS

Extended European Search Report issued in connection with corresponding European Patent Application No. 22182603.5, Dec. 13, 2022, 11 pages.

* cited by examiner

SURGICAL DISTRACTOR AND METHODS OF MANUFACTURE AND USE

CROSS-REFERENCE TO RELATED APPLICATION

This application claims priority under 35 U.S.C. § 119(e) to U.S. Provisional Application No. 63/232,305, filed on Aug. 12, 2021, the entire contents of which are incorporated herein by reference.

TECHNICAL FIELD

The disclosure relates to surgical instrument used to displace tissue and methods of manufacture and use thereof in orthopedic procedures. Surgical instruments, for example, distractors, are described herein that may be capable of maintaining a desired displacement of tissues determined to be necessary based on the type of procedure and/or anatomy of a patient. For example, a distractor may be used to maintain a predetermined displacement during a surgical procedure without requiring a member of a surgical team, in particular a surgeon, to maintain contact with the distractor. This may allow a surgical team, and in particular, a surgeon, to maintain a predetermined displacement of the tissues while simultaneously conducting additional procedures such as drilling and inserting screws.

BACKGROUND OF THE INVENTION

Orthopedic surgeries can be complicated and time consuming procedures that often require surgical teams to work in a confined space with little room to maneuver. Examples of such procedures that may require displacement of bone by the surgeon may include osteotomies, for example, bi-cortical osteotomies in the foot or hand, Chevron osteotomy, distal or proximal metatarsal or metacarpal osteotomies, Weil osteotomy, and/or fixation of osteotomies for Hallux Valgus treatment (such as Scarf, Chevron, etc.). Minimally invasive Chevron and Akin (MICA™) procedures, for example, may require a surgeon to displace a section of target bone, as shown in FIGS. 1-2. In conventional procedures, this displacement may be the result of positioning an elevator 24, 28, 30 and fixing an elongated member 22, as shown in a radiograph in FIG. 2 and FIGS. 3A-B. Generally, a surgeon displaces an osteotomy using a common periosteal elevator. To maintain the desired displacement, the surgeon must hold the elevator in position while drilling and inserting screws since there is no way to maintain the displacement without leverage provided by the surgeon. This generally requires two hands and can make it difficult to perform in the confined space of a surgical theater.

SUMMARY OF THE INVENTION

A surgical instrument may be used to displace tissue and maintain this displacement during a surgical procedure. Such a surgical instrument may be a distractor and include holder portions coupled together using one or more coupling elements.

A medical instrument as described herein may include one or more holder sections. In particular, a medical instrument may include a first holder section and a second holder section coupled to the first holder section using one or more coupling elements. The coupling elements may be coupled to both the first holder section and the second holder section.

The holder sections may include one or more displacement elements. For example, each of a first holder section and a second holder section may include displacement elements that engage each other. Further, the first holder section may include a positioning element while the second holder section may include a rotatable component that includes an opening.

Positioning of the holder sections may be controlled by the surgeon. In particular, positions of a first holder section relative to a second holder position may be controlled by a hand position of the user. In some instances, the holder sections may include handle elements. For example, handle elements similar to those on scissors or pliers may be used on a distractor. A distractor may include a handle section that includes scissor-style handles and/or plier-style handles.

Coupling elements may be used to couple holder sections. For example, a distractor may include coupling elements such as a bar coupled to both the first and second holder sections. In some instances, multiple coupling elements such as bars and/or fasteners, may be used to couple holder sections. In some instances, coupling elements may be coupled to the holder sections and/or one or more bars.

In some instances, a distractor may include a movable member such as a screw to control a position of a first holder section relative to a second holder section. In some embodiments, a positional screw may be configured to control the distance between holder sections by adjusting coupling elements. For example, a positional screw may be configured to control the distance between holder sections by adjusting a four-bar linkage that couple the holder sections together.

A distractor may include a movable member that is capable of controlling a position of the tissue-engaging element relative to the rotating component. One or more movable members including bars and/or fasteners may be used to form a four-bar linkage that controls movement of the tissue-engaging element and the rotating component.

Holder sections on a distractor may include displacement elements. Displacement elements may include ratchet mechanisms, pawls, racks and/or tooth element, for example, a rack with teeth.

Another embodiment of a medical instrument, such as a distractor, may include a handle section, one or more coupling elements, a tissue-engaging element, and a rotating member that includes an opening. In some instances, a rotating member may include a pin component. A pin component may be used to limit movement of the rotating member. Distractors may include a ratchet mechanism. Ratchet mechanisms may maintain a desired position of the distractor once set.

Various embodiments of the distractors disclosed herein may be used in methods of distracting tissue during surgery. Distractors for use in surgery to distract tissue may include a guide and/or a locking member. For example, during a surgical procedure an initial incision may be made at a target area of a patient. In some instances, an osteotomy may be created proximate the target area by a surgeon. Members of a surgical team may position a wire into a medullary canal of a proximal portion of a metatarsal of the patient. At this point, the surgical team may position a distractor proximate the target area. A locking member may engage a positioning wire to reversibly fix the wire relative to the medical instrument.

During a surgical procedure, elements of an instrument may be moved such that holder sections are positioned to allow the tissue-engaging portion to be positioned in a desired position relative to a patient's target area and/or a rotating member of the instrument. After positioning in the desired position a member of the surgical team, such as a surgeon, may engage a locking mechanism to secure the instrument such that a desired displacement is maintained without further intervention by a member of the surgical team.

Movement of the holder sections relative to each other allows the instrument, that is, the distractor, to maintain the desired displacement of the osteotomy. In some embodiments, the distractor may include a locking mechanism to maintain the desired displacement of the osteotomy. For example, a locking mechanism may include a ratchet. Desired displacement of tissues may occur near a target area of the patient. For example, it may be desired to fix at least a portion of tissue near the proximal end of a metatarsal during a surgical procedure. In some embodiments, a medical device may include a tissue-engaging portion positioned on a holder section configured to engage a patient's target area. Another holder section may include a rotatable component having an opening configured to engage a positioning element.

Maintaining a desired or predetermined displacement of tissues using a distractor may involve engagement of a first displacement element positioned on the first holder section with a second displacement element positioned on the second holder section. The displacement elements may be configured to engage each other such that a desired and/or predetermined distance is maintained between the positioning element and the rotatable component.

In some embodiments, medical distractors may include a tissue-engaging portion positioned on a first holder section and a rotatable component having an opening and positioned on a second holder section. Displacement elements positioned on the holder sections are constructed such that they can engage each other. Further, the displacement elements may be configured to engage each other such that a predetermined distance is maintained between the tissue-engaging portion and the rotatable component.

In some embodiments, the displacement elements may include elements of a mechanism. For example, a displacement element may be a bar positioned along the bottom of the handle components as is commonly used with other surgical instruments. Some embodiments of a distractor may include a pin component permanently affixed to a rotatable component on a handle portion.

Utilizing computer-assisted surgery and/or minimally-invasive systems may improve outcomes for patients by allowing for the use of patient-specific methods, instruments, and/or devices. In particular, orthopedic surgeries are complicated and time consuming and any steps that can be removed or combined may decrease surgical time, thereby potentially reducing infection risk for the patient and likely increasing patient and/or doctor satisfaction.

Materials used in distractors and/or elements thereof may be selected based on properties such as compatibility with in vivo use, strength such as yield strength and/or ultimate strength, Young's modulus, creep/viscoelasticity, fatigue, resistance to abrasive wear, compatibility with post-processing procedures such as cleaning, and sterilization and/or other properties of interest, and/or properties that affect ease of manufacturing such as material machinability and/or ease of use in molding. Materials of interest for use in distractors and/or elements thereof may include but are not limited to metals such as titanium, tantalum, and niobium, alloys like stainless steel, cobalt-chromium alloys, titanium alloys, aluminum alloys, and/or nitinol, plastics such as polycarbonate (PC), polyethylene (PE), methyl methacrylate (MMA), polymethyl methacrylate (PMMA), polyether ether ketone (PEEK), poly ether ketone ketone (PEKK), acrylonitrile butadiene styrene (ABS), polylactic acid (PLA), hydroxyapatite, ceramics such as calcium phosphate ceramics, carbon-based materials such as carbon fiber, graphite, and/or graphene. In some embodiments, it may be desired to use a material having a hardness selected based on the requirement of use.

For patient-specific surgeries, surgical planning for sizing and alignment may be performed pre-operatively based on x-rays, computed tomography (CT), magnetic resonance imaging (MRI) or another three-dimensional (3D) medical imaging dataset, usually in a 3D computer aided design (CAD) environment. Based on the planned location and alignment of the respective implants, the surgical alignment guide may be designed to replicate the planned implant alignment in concert with the other surgical preparation instruments by fitting over the patient's bone and/or cartilage in one specific position based on the topography of the patient's anatomy. As an additional intra-operative check using imaging, such as fluoroscopy, may be useful in confirming that the location of the alignment guide has been achieved to the surgeon's satisfaction. Such an ability to check the alignment of the guide early in the surgical procedure, prior to fully committing to the placement of the alignment guide, may reduce the risk of improperly preparing the bone and give the surgeon an opportunity to find a location and alignment of the guide that meets their expectations.

Use of a combination of pre-operative planning, additive manufacturing, such as 3D printing capabilities, and/or molding may allow use of instruments, such as a distractor including a section that may conform to the patient's anatomy. Matching surfaces of a device to a patient, in particular, to the natural anatomical surface contour of a patient's bone, may ensure a better fit during surgery. For example, using a distractor that has a geometry on the tissue-engaging section that conforms or at least partially conforms to a target area may allow for more accurate and secure positioning of elongated members such as wires, k-wires, and/or pins and/or fasteners such as screws.

A device may be formed from a patient-specific component and a standard body component coupled in a manner that allows them to be permanently coupled or temporarily coupled, for example, the standard body component may be separated from the patient-specific component such that the standard body component may be reused. In some instances, the patient-specific component and the standard body component may be affixed permanently to each other during an assembly manufacturing step using couplers including, but not limited to, fasteners, adhesives such as glue, etc., and combinations thereof.

Disclosed embodiments may be used in a variety of applications and methods, including surgical methods for operating on a patient and, in particular, on a patient's hand and/or foot. Material selection may also be influenced by the design of an instrument and/or elements thereof. In particular, size of the instrument and/or elements and/or the desired fit between the instrument, elements, and/or the target area may necessitate use of specific materials to meet the requirements of use.

Materials for use in instruments described herein may be selected based on desired material properties. Materials such as metals, alloys, ceramics, plastics, and/or combinations thereof, can be used in concert to meet the required properties of the instrument, and/or suitability for use in manufacturing processes such as molding, 3D printing such as stereolithography, selective laser sintering, and/or the like. In some instances, some of the materials used to form at least a portion of the instrument may be radiolucent.

For example, an instrument that includes radiolucent materials may enhance the ability of a surgical team to position the instrument proximate a target area during a surgical procedure. In some instances, it may be desirable for a tissue-engaging portion of the instrument to have a specific geometry. For example, in some instances the tissue-engaging portion may have a geometry that complements the geometry of the tissues to be distracted. In particular, a tissue-engaging portion may have a surface that is complementary to the surface topology of bone at the target area.

Although the invention has been described in terms of exemplary embodiments, it is not limited thereto. Rather, the appended claims should be construed broadly, to include other variants and embodiments of the invention, which can be made by those skilled in the art without departing from the scope and range of equivalents of the invention.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts, and further wherein.

DETAILED DESCRIPTION OF PREFERRED EMBODIMENTS

Figure 1:
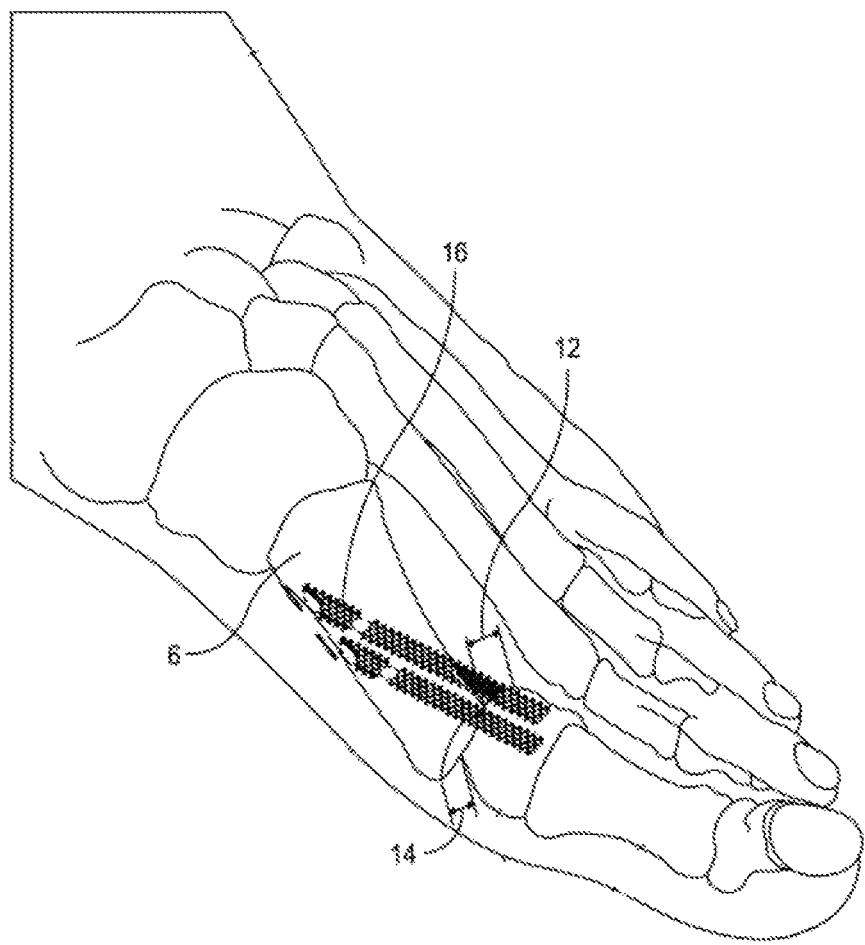
FIG. 1 depicts a perspective a view of a foot that has undergone a surgical procedure involving displacement of bone and subsequent fixation of the displaced bone.

This description of the embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Disclosed embodiments include a distractor for use in orthopedic surgery. Distractors may be used to position tissue, such as bone. Use of a distractor may allow a surgical team, and in particular, a surgeon to maintain a predetermined displacement of tissues while simultaneously conducting additional procedures such as drilling and inserting screws. More specifically, a distractor may be capable of maintaining a selected displacement between tissues, by separating the bones and then locking the linkage using a screw, without requiring a surgeon or other team member to hold the distractor after placement and thereby allowing the surgeon and team members to freely position other instruments and/or devices related to the surgical procedure.

Bones and/or portions thereof may be positioned relative to one another in a predetermined configuration to correct a problem area. In particular, hallux valgus deformities may be corrected using a Chevron Osteotomy. Corrective positioning may be achieved after one or more bones or portions thereof are displaced and then held in place by fasteners. Referring to FIG. 1, corrective positioning is achieved after a portion of the metatarsal bone 6 is displaced a displacement distance 12, 14 and then held in place by fasteners, e.g., screws 16. Displacement 12, 14 is maintained throughout such a procedure to allow proper positioning of securing elements, such as screws.

Figure 2:
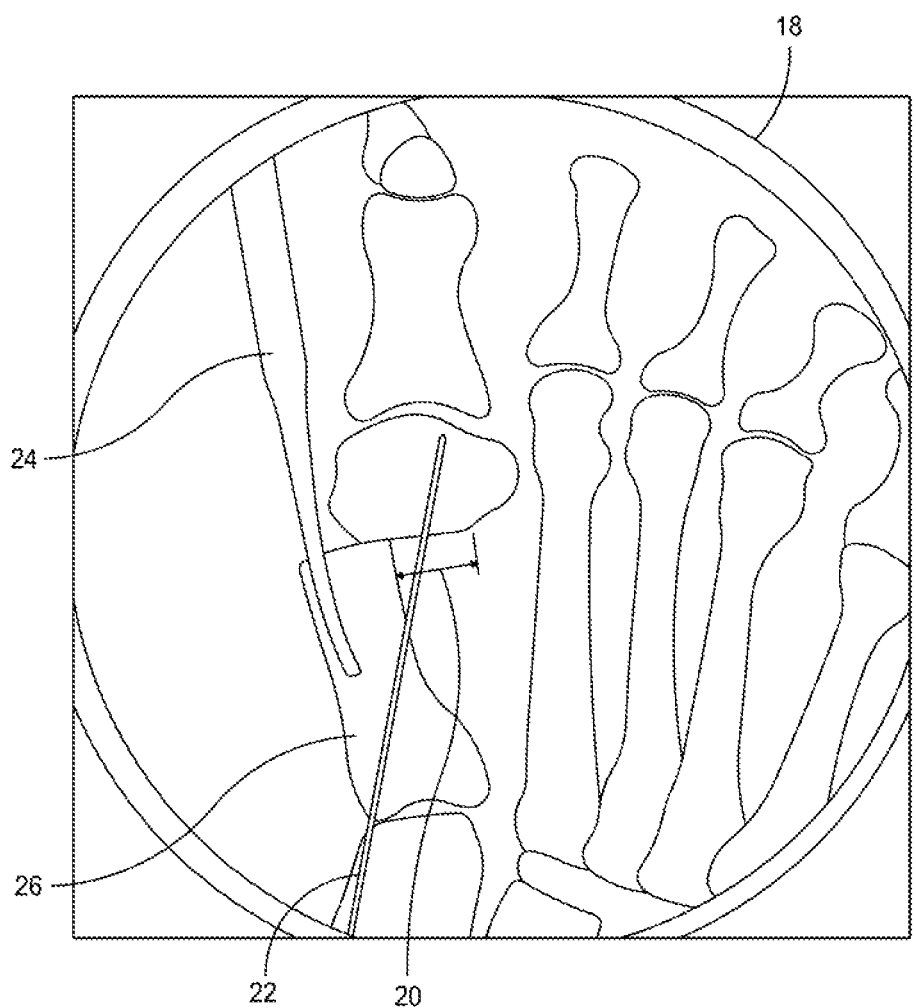
FIG. 2 is a drawn representation of a typical radiograph image of a foot as viewed during a surgical procedure involving displacement of bone.
Figure 3A:
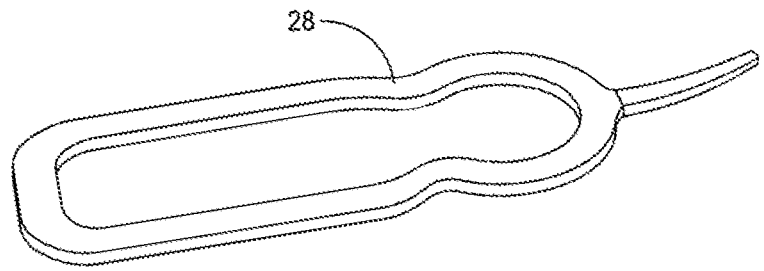
FIG. 3A depicts a perspective view of an elevator used to displace tissue, such as bone, during surgery.
Figure 3B:
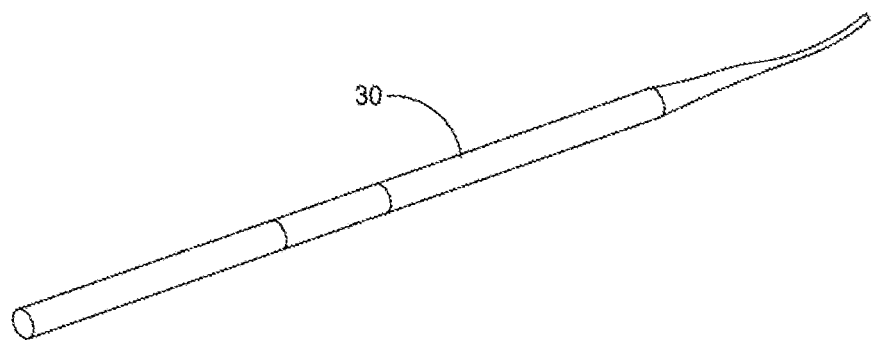
FIG. 3B depicts a perspective view of another surgical elevator used to displace tissue, such as bone, during surgery.

Displacement 20 of a portion of metatarsal bone 26 is represented in a drawing depicting an X-ray image 18 of FIG. 2 using conventional elevator 24. Images of elevators 28, 30 used in conventional procedures are shown in FIGS. 3A-3B.

Figure 4:
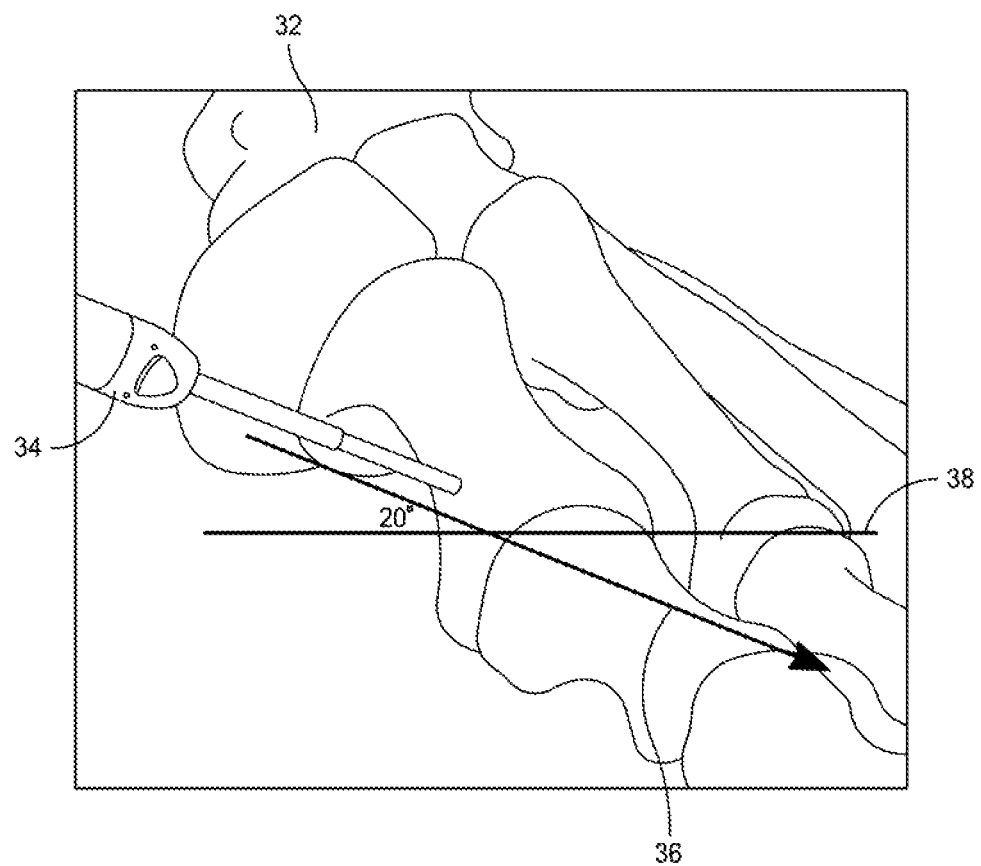
FIG. 4 depicts an image of bones in the foot and a Burr positioned along a desired plane.

Referring to FIG. 4, foot 32 with burr 34 may be aligned to desired potential planes 36, 38 for an osteotomy, according to known procedures. Generally, a burr should be positioned perpendicular to a plane extending along the first metatarsal and angled at a 20 degree angle as shown in FIG. 4.

Figure 5:
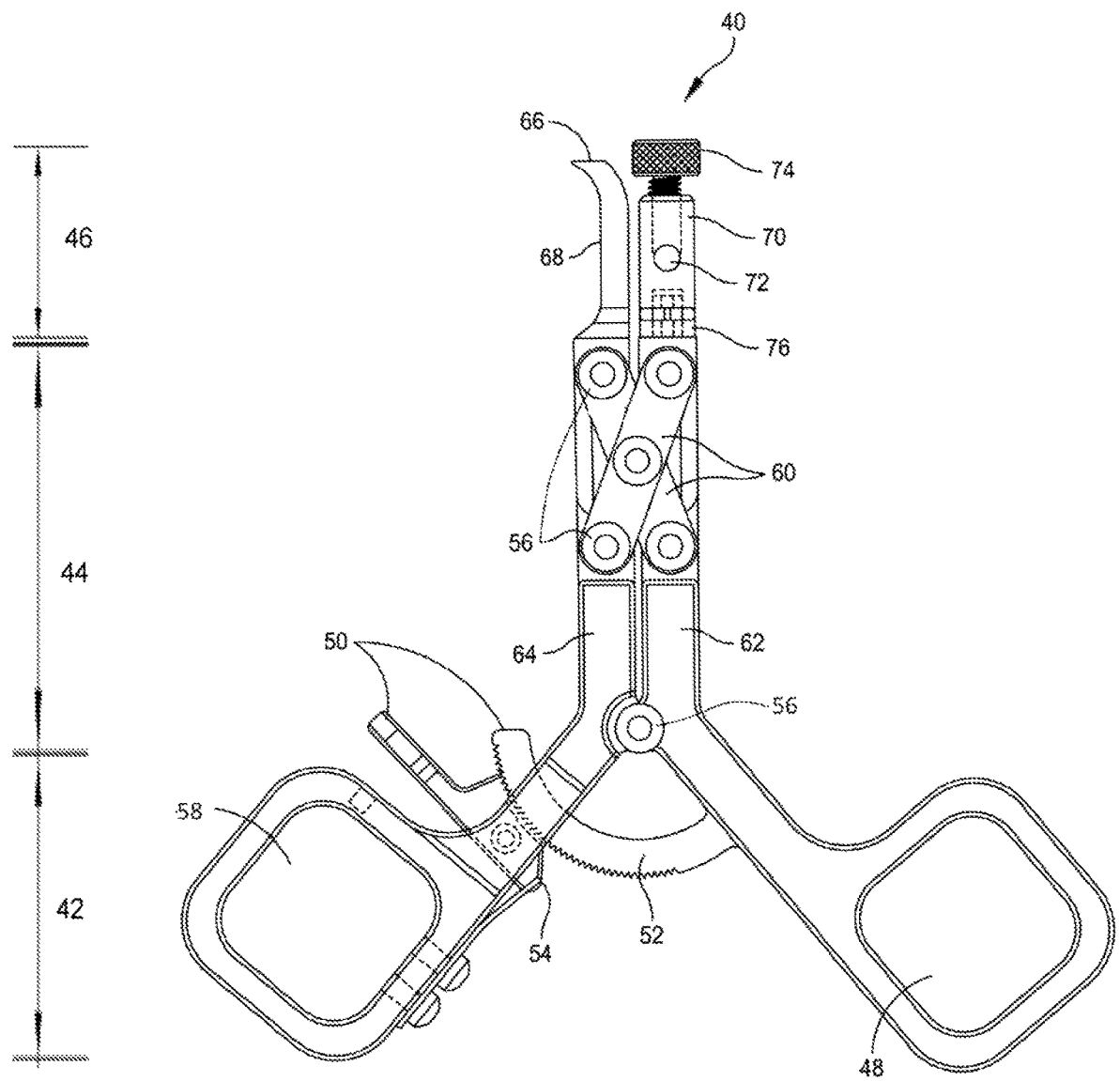
FIG. 5 depicts a plan view of a distractor of one embodiment of the invention in a pre-distraction configuration.

Distractors of the invention as described herein are shown in FIGS. 5-12 for use in various surgical procedures. Referring to FIG. 5, distractor 40 in a pre-distraction configuration includes sections 62, 64 that are divided into handle portion 42, coupling portion 44, and engaging portion 46. Handle portion 42 includes openings 48, 58 and ratchet mechanism 50. Ratchet mechanism 50 includes displacement elements, including pawl 54 and rack 52. As depicted, section 64 includes pawl 54 and section 62 includes rack 52. In some embodiments, pawl 54 and rack 52 may be configured to releasably engage each other. For example, pawl and rack may include engaging members such as teeth.

Coupling portion 44 includes coupling elements 56. Coupling elements 56 may be fasteners as shown in FIG. 5. Fasteners may include, but are not limited to, screws, rivets, pins, bolts, other known fasteners in the art and combinations thereof. Coupling elements 56 may include elongated member 60 as shown in FIG. 5. Elongated members 60 may be formed such that they can be coupled together by coupling elements 56 and to both sections 62, 64 of the distractor device 40. In some embodiments, coupling portion 44 has been formed using a closed-chain movable linkage, such as a four-bar linkage, with advantageous results.

Engaging portion 46 may include tissue-engaging portion 68 and fixation portion 70. Fixation portion 70 may include opening 72, locking member 74 and rotating member 76. As shown in FIG. 5, rotating member 76 includes opening 72 and locking member 74 in the form of set screw. In some embodiments, the locking member or set screw 74 may communicate with the opening 72. For example, a set screw may extend through the rotating member and potentially into the opening. Tissue-engaging portion 68 may have a geometry selected by a surgical team based on the procedure to be performed, the anatomy of a patient, and/or other reasons determined by the surgical team, such as tip 66 of engaging portion 46.

Figure 6:
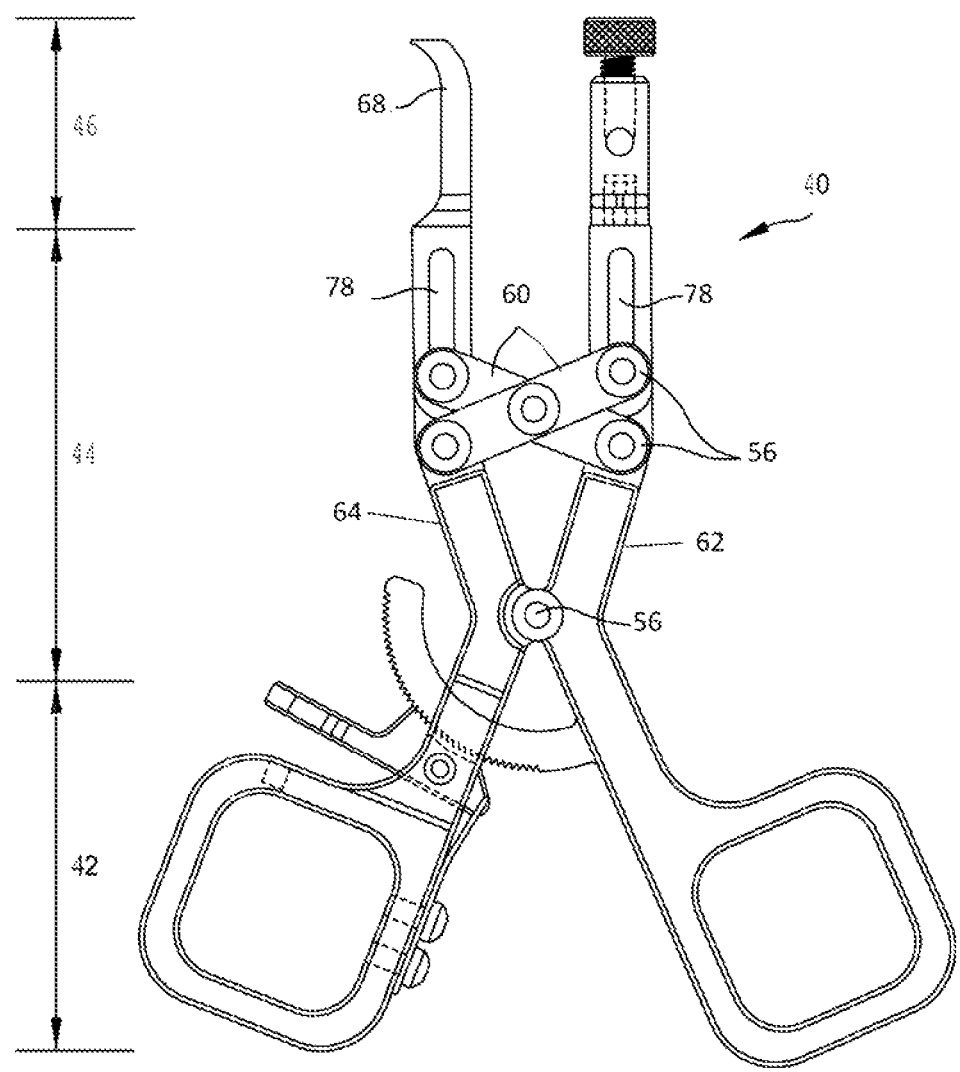
FIG. 6 depicts a plan view of the distractor as shown in FIG. 5, but in a post-distraction configuration.

Distractor 40 is shown in FIG. 6 in a post-distraction position. Sections 62, 64 of distractor 40 are separated as they would be during use. This capability to separate allows the distractor 40 to provide the predetermined displacement distance during use. Corrective positioning may be achieved after the distractor 40 is positioned proximate a target area. Tissue-engaging portion 68 is configured to engage with a target area during a surgical procedure. In some embodiments, a distractor may have a tissue-engaging portion with a geometry selected based on a surgical procedure, an anatomy of a patient, and/or other desired properties as determined by a surgeon or a member of a surgical team. In some embodiments, a distractor 40 may be maintained in a post-distraction position, maintaining a selected displacement between tissues, by separating the bones and then locking the linkage using a screw 74, without requiring a surgeon or other team member to hold the distractor after placement.

As shown in FIG. 6, coupling portion 44 includes coupling elements 56 and elongated members 60. Elongated members 60 are pivotally coupled to one another and to both sections 62, 64 of the distractor device 40. Sections 62, 64 includes openings 78 in which coupling elements 56 are positioned. Coupling elements 56 may be moved in the openings 78 to control positioning of the elongated members 60 and thereby of the opposing sections 62, 64 of the distractor 40. Openings 78 may be used to control movement of the sections 62, 64 of the distractor 40. For example, openings may guide elongated members due to the position of fasteners within the openings. Openings 78 may have a geometry selected based on a path that the openings 78, fasteners 56, and/or elongated members 56 allow sections 62, 64 of the distractor 40 to travel. These may be selected based on the type of procedure, the anatomy of the patient and/or other requirements of the surgical team.

Figure 7:
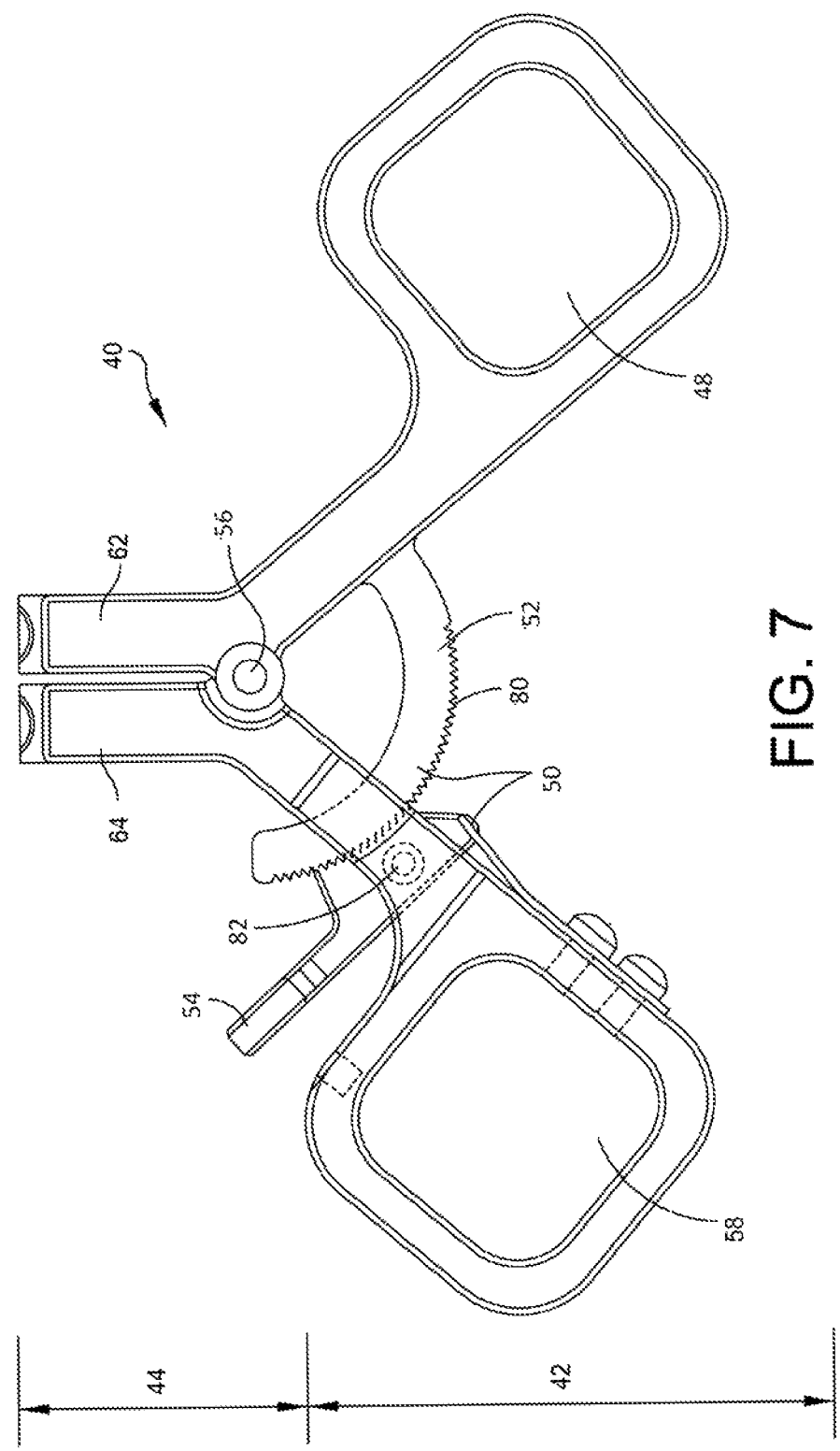
FIG. 7 depicts an enlarged view of a handle portion and a ratchet mechanism of the distractor as shown in FIG. 5.

FIG. 7 depicts a partial view of distractor 40 in a pre-distraction mode that includes sections 62, 64 pivotally coupled together by fastener 56. Distractor 40 includes handle portion 42 and part of coupling portion 44. Handle portion 42 includes openings 48, 58 and ratchet mechanism 116. Ratchet mechanism 50 includes displacement locking elements, including pawl 54 and rack 52. Section 64 includes pawl 54 and section 62 includes rack 52 having teeth 80 arranged and oriented so as to operatively engage pawl 54. Pawl 54 and rack 52 may be configured to releasably engage each other. In some instances, rack 52 may be formed integrally with section 62. Portions of pawl 54 may be secured to section 64 using fasteners. At least one fastener (shown as 82) may allow pawl 54 to rotate and engage rack 52.

Figure 8:
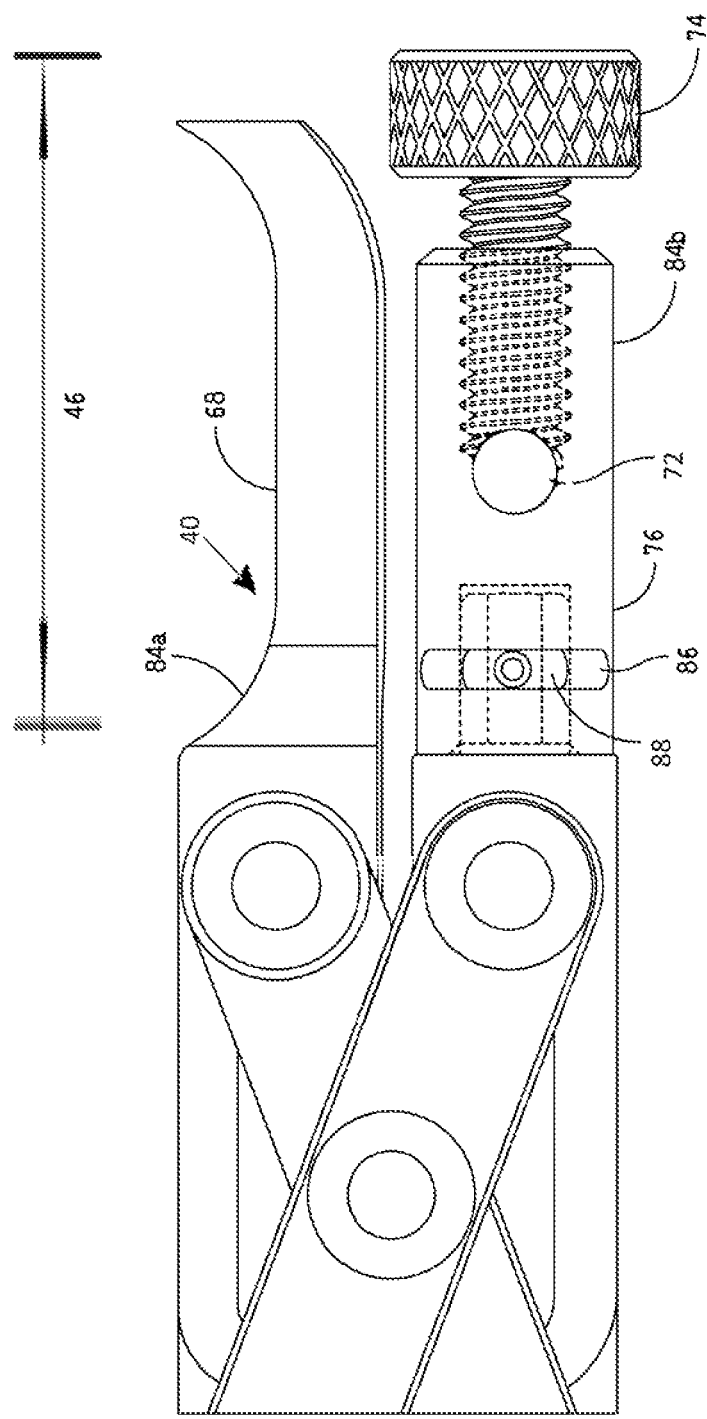
FIG. 8 depicts an enlarged view of a distractor portion and coupling elements of the distractor as shown in FIG. 5.

Referring to FIG. 8, engaging portion 46 includes tissue-engaging portion 68 and first fixation portion 84a. Tissue-engaging portion 68 includes radiused surface defined on first fixation portion 84a. In some embodiments, the tissue-engaging portion 68 may include a surface that is configured to engage a target area of a patient. For example, a tissue-engaging portion may include a radiused surface on a first fixation portion shaped like a cup to engage a bunion deformity on a patient's foot. In some instances, the tissue-engaging portion 68 may have a surface on first fixation portion 84a shaped to engage a lateral side surface of a patient's foot or a portion thereof. For example, a tissue-engaging portion may have a surface on a first fixation portion shaped to engage a lateral aspect of a calcaneal tuberosity.

Figure 9:
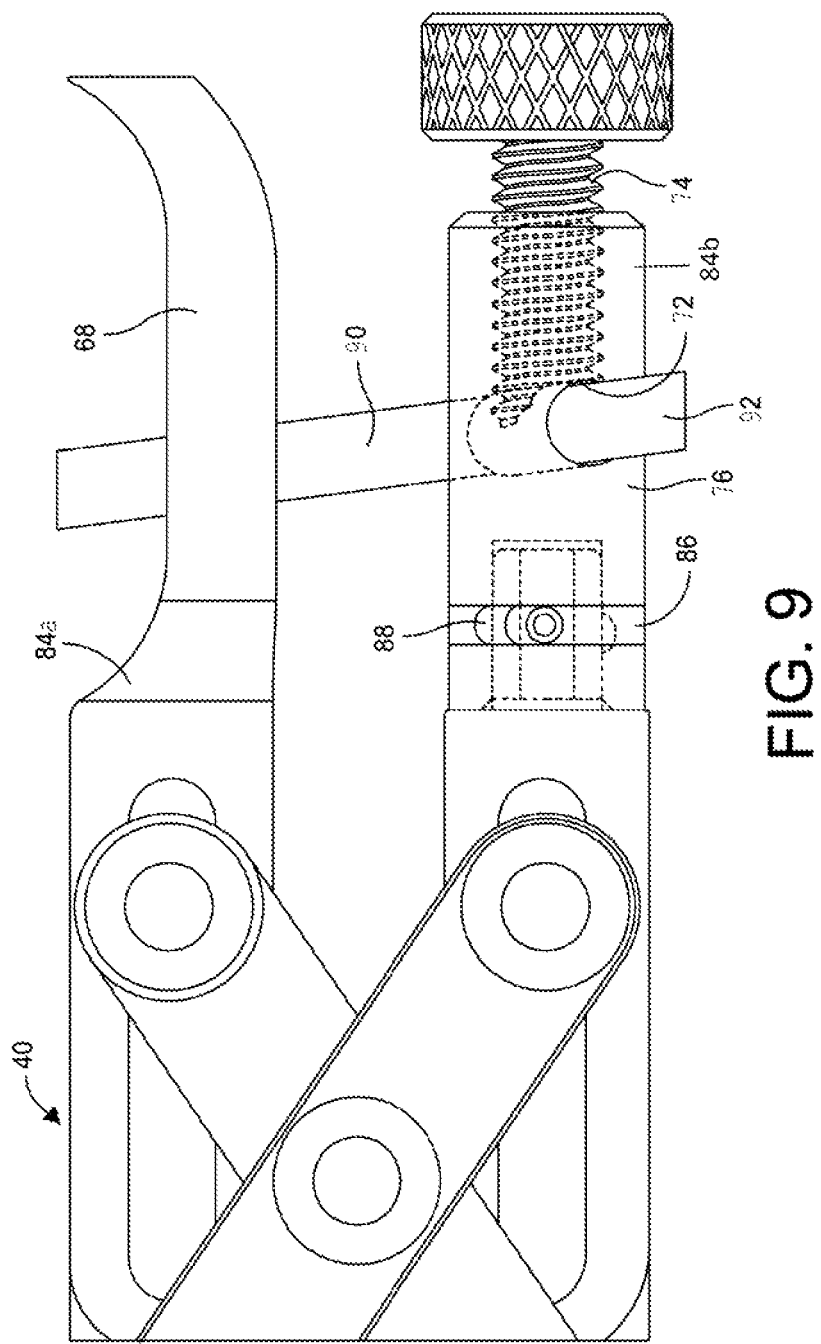
FIG. 9 depicts an enlarged view of the distractor portion and coupling elements of the distractor as shown in FIG. 5, but in a post-distraction configuration.

A second fixation portion 84b may include opening 72, locking mechanism 74, rotating member 76, and member 88 positioned in slot 86. Member 88 may be moved within slot 86 such that it allows or inhibits rotation of the rotating member 76. In this manner, the opening 72 in the rotating member 76 may be positioned as desired with respect to a target area. Further, rotating member 76 may include opening 72 and set screw 74. For example, a set screw may extend through a rotating member and potentially into an opening. As shown in FIG. 9, set screw 74 threadingly engages opening 72 so as to press an outer surface of wire 90 positioned within opening 72. For example, a screw set a engages wire such that a distractor is fixed during use. In particular, the set screw 74 may clamp any element placed in the opening 72, such as a k-wire 92, to inhibit and/or prevent movement of the distractor 40 relative to any element during use. For example, a set screw that communicates with an opening may prevent or inhibit movement of a distractor relative to a wire in an opening.

The slot 86 may allow the rotating member 76 to rotate as needed to allow for a desired positioning of the distractor 40 and/or elements coupled to the distractor 40. For example, a desired positioning of wires may be achieved after a distractor is positioned due to the possible rotation of a rotating member, as well as the positioning of a wire in an opening. In some instances, the degree of rotation may be limited to a predetermined range based on the requirements of use.

Figure 10:
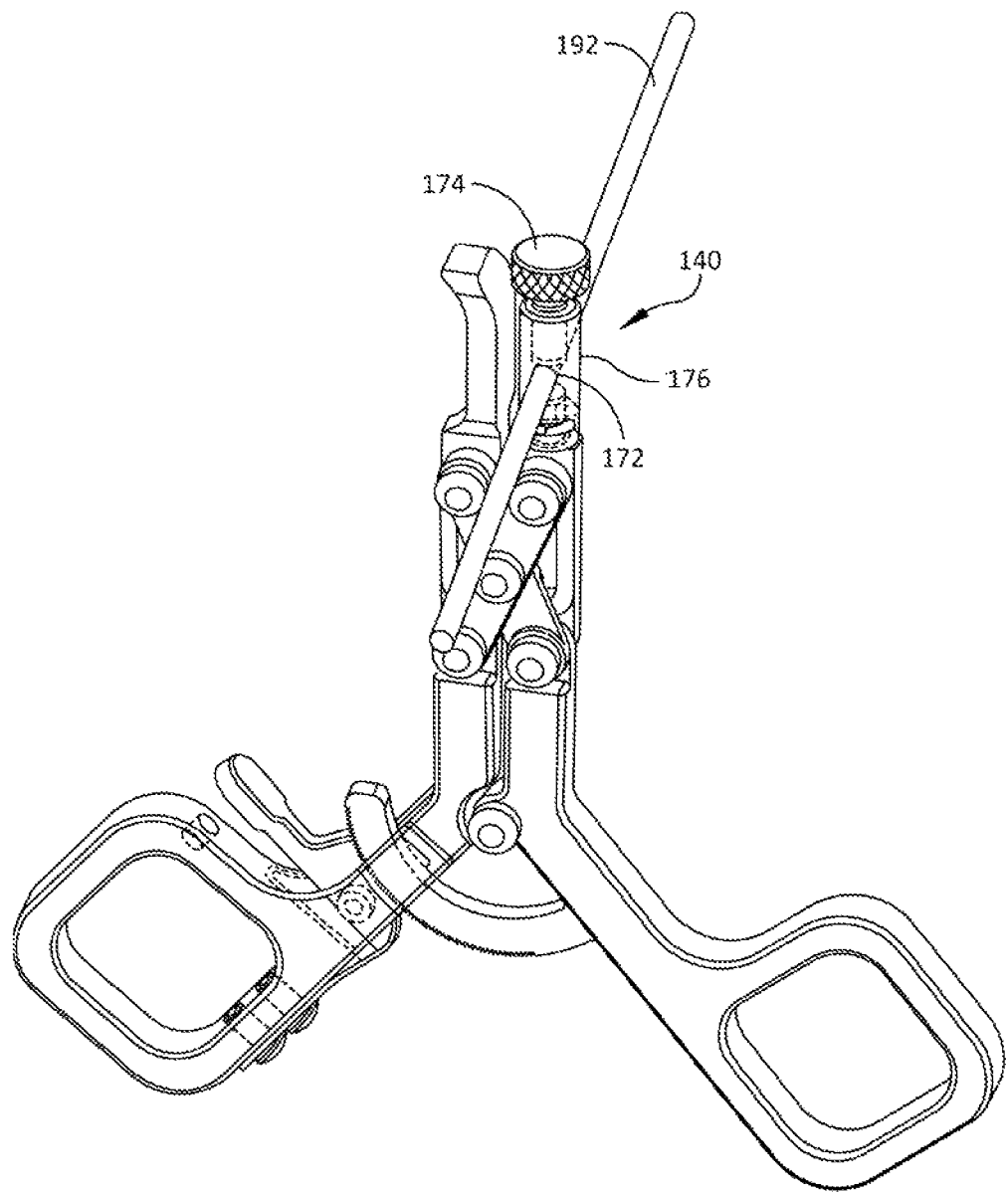
FIG. 10 depicts a perspective view of a distractor of one embodiment of the invention in a pre-distraction configuration coupled to an elongated member.

Referring to FIG. 10, a distractor 140 is arranged in pre-distraction mode having elongated member 192 positioned in opening 172, as required by the surgical procedure, the surgical team, and/or the anatomy of the patient. Elongated member 192 may be movable within opening 172 so long as set screw 174 has not yet been secured against a portion of it. Rotating member 176 has been rotated such that the elongated member 192 is positioned at a desired angle relative to a plane extending through the distractor 140.

Figure 11:
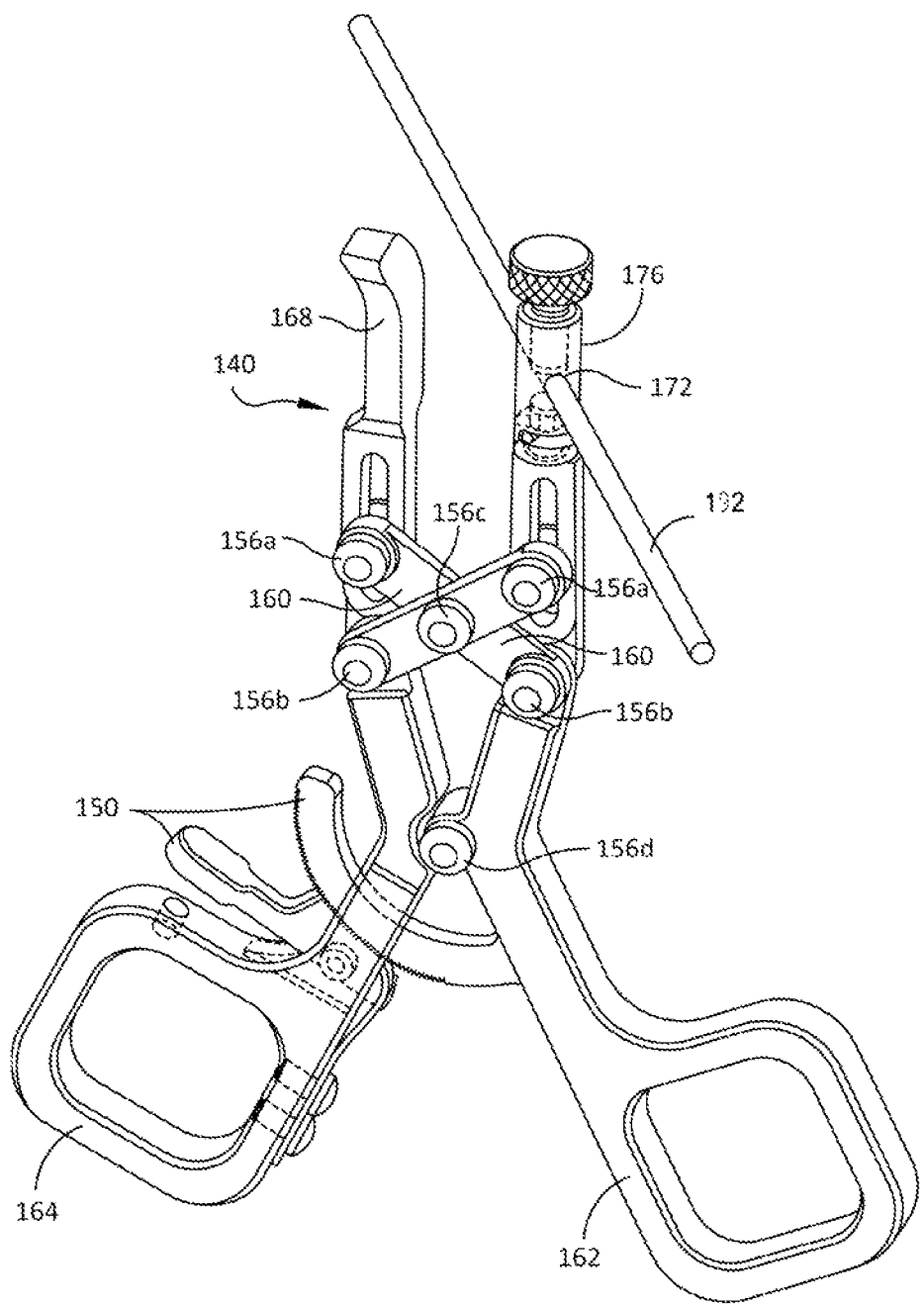
FIG. 11 depicts a perspective view of the distractor as shown in FIG. 10, but in a post-distraction configuration coupled to the elongated member.

Referring to FIG. 11, distractor 140 is shown in a position which allows for a displacement of tissue to be maintained. Rotating member 176 is rotatable as the distractor 140 is moved into a position that allows for displacement of tissue. For example, as a distractor is moved into position, a rotating member rotates such that angulation of, e.g., a metatarsal, is positioned as required by the surgeon. A ratchet mechanism 150 is used to lock the distractor 140 in a surgeon desired position. In some embodiments, for example, a surgeon may separate the bones and then lock the linkage, so as to maintain the bone separation selected, using a screw set (e.g., a thumb screw, set screw 174, etc.). Engaging the ratchet mechanism 150 may allow the surgeon and/or other members of the surgical team to take hands off distractor 140, when in the locked position, during the surgical procedure to do other tasks related to the surgical procedure. As shown, rotating member 176 may be rotated as distractor 140 is moved into a position that allows for displacement of tissue.

Figure 12:
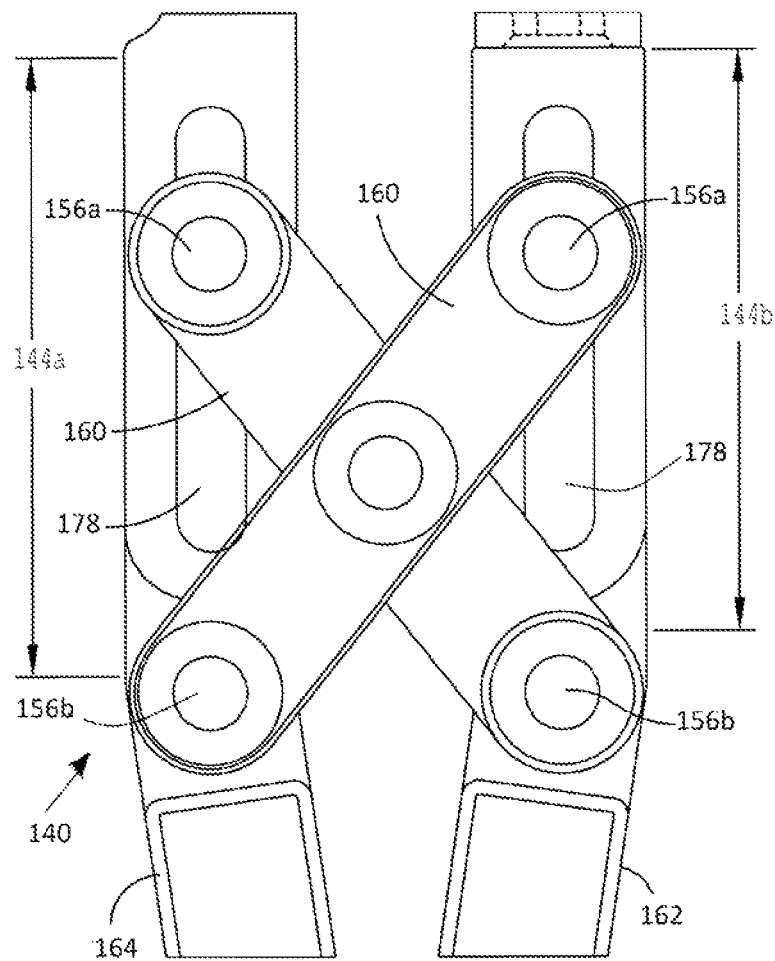
FIG. 12 depicts an enlarged view of coupling elements of the distractor as shown in FIG. 10, but in a slightly distracted distraction configuration.

Referring to FIG. 12, elongated strut members 160 are in a position where distractor 140 may be slightly distracted. Elongated strut members 160 act as coupling elements along with fasteners 156a, 156b so as to couple the elongated strut members 160 to sections 162, 164 to form a four-bar linkage, such that the elongated strut members 160 may move when a screw set (not pictured here) is released. Fasteners 156a are positioned within slots 178 such that they are allowed to slide along slots 178 such that sections 162, 164 are moved in manner that will allow sections 144a, 144b to be maintained in a substantially parallel configuration relative to each other during movement. For example, fasteners 156a, 156b may move along slots 178 to ensure that sections 144a, 144b, as shown in FIG. 12, are parallel.

Referring once again to FIG. 11, the elongated strut members 160 may allow the distractor 140 to move such that planes running through a midline of the patient engaging portions of distractor 140 are substantially parallel to one another. In some embodiments, the distractor 140 includes an attachment mechanism for a vertical Kirchner wire ("k-wire") 192 or some other elongate straight slender rod to be used as a physical visual reference and/or positioning element. One embodiment includes wire 192 (e.g., Kirchner wire) for aligning the distractor 140 with respect to the patient and/or providing a visual check. FIGS. 9-11 illustrate an embodiment in which the Kirchner wire 92, 192 is positioned in opening 72, 172 of rotating member 76, 176 of distractor 40, 140.

Bone engaging portions may have a geometry selected by a surgical team based on the procedure to be performed, the anatomy of a patient, and/or other reasons determined by the surgical team. For example, as shown in FIG. 11, bone engaging portion 168 has a geometry selected to engage with a bunion deformity, lateral calcaneal tuberosity, and/or outer surface of a foot.

Elongated members as disclosed herein above may couple separate sections of a distractor together. Sections of the distractor may be formed as separate elements and coupled together. For example, sections of a distractor may be coupled using a combination of fasteners such as screws, rivets, pins, bolts, other known fasteners in the art and/or elongated members such as struts, bars, etc. As shown in FIG. 11, sections 162, 164 of distractor 140 are coupled to one another by fastener 156d. Further, elongated strut members 160 are coupled to sections 162, 164 using fasteners 156a, 156b. Elongated strut members 160 are coupled to each other by fastener 156c. Openings in sections may be positioned to control movement of the sections relative to each other such that planes running through a midline of the engaging portions are substantially parallel to each other.

Materials for the body sections may include radiolucent materials. Body sections may include composites, thermoplastics, including, but not limited to, polycarbonate (PC), polyethylene (PE), methyl methacrylate (MMA), polymethyl methacrylate (PMMA), polyether ether ketone (PEEK), poly ether ketone ketone (PEKK), acrylonitrile butadiene styrene (ABS), polylactic acid (PLA), polyamide, such as nylon, other plastics known in the art, and combinations thereof. In particular, materials may be selected that are capable of being used in additive manufacturing, such as 3D printing, selective laser sintering (SLS), and/or injection molding, for example polyamides, such as nylon or ceramics. In some embodiments, materials used in an instrument may be selected for specific properties desired in a particular instrument or location in the instrument such as magnetism, surface roughness, reflectivity, refractivity, radiolucency, radiopacity, strength, compatibility with in vivo placement, etc.

A surgical procedure utilizing embodiments of a distractor 40, 140 begins with the distraction of tissue during surgery after an initial incision at a target area of a patient. The surgeon creates an osteotomy of the metatarsal, proximate to the target area. The surgeon then positions a wire in an intramedullary canal of a proximal portion of a metatarsal of the patient. The distractor 40, 140, with a guide and a locking member 74, 174 (i.e., set screw) is then positioned proximate the target area such that the wire is positioned in the guide of the distractor 40, 140. The locking member 74, 174 is turned until it engages the wire 92, 192 positioned in the guide such that the wire 92, 192 is not capable of sliding within the guide due to the frictional engagement between the screw 74, 174 and the wire 92, 192. Essentially, the locking member 74, 174 is used to reversibly fix the position wire 92, 192 relative to the distractor 40, 140. Holder sections 62, 64, 162, 164 are moved such that the desired position of the tissue-engaging portion 68, 168 is achieved. Thus, the locking mechanism 74, 174 secures the distractor 40, 140 in a desired position such that a desired displacement was maintained without further adjustment by the surgeon. When the locking mechanism 74, 174 secures the distractor 40, 140 in the desired position, so as to maintain the bone separation selected, the surgeon's hands free-up to do other tasks related to the surgical procedure. For example, the surgical procedure disclosed herein utilizing a distractor 40, 140 for a Chevron Osteotomy may be used to correct a hallux valgus deformities. A stab incision first placed over the dorso-medial aspect of the proximal edge of the 'flare' of the medial eminence. The incision is placed such that it avoids the dorso-medial cutaneous nerve to the Hallux.

Once the incision is made, a distractor 40, 140 is used to carefully create a working area for a burr (not shown). The space is created over the dorsal surface of M1, but not on the plantar surface, as this may risk damage to the blood supply of the M1 head. An osteotomy is created with the burr, e.g., the dorsal aspect of the osteotomy is created using a 2×20 mm burr placed into the stab incision portal and onto the exposed bone surface. Once the burr exits the lateral cortex of the metatarsal, a portion of the burr is rotated and lifted so that the burr cuts dorsally. The plantar limb is created by placing the burr back into the original bi-cortical position. Then, under controlled power, the burr is translated plantarly and simultaneously a hand piece is rotated dorsally and/or laterally (so the burr moves in a plantar medial direction) until the burr exited the medial cortex. After completing the plantar osteotomy, a hand piece is positioned dorsal to the hallux to ensure the burr has fully exited the medial cortex of the metatarsal. Once the cut is complete (confirmed by the motion at the osteotomy site), the metatarsal head is displaced along its defined plane.

Displacement of the bone is achieved by placing a wire 92, 192 through the existing portal. A distractor 40, 140 is then applied over wire 92, 192 and actuated to leverage the distal fragments laterally. In particular, distractor 40, 140 is positioned such that the tissue-engaging portion 68, 168 and fixation portion 70, 84*a*, 84*b* are proximate the target area such that the wire 92, 192 is positioned in the guide; engaging the locking member 74, 174 such that the position wire 92, 192 is reversibly fixed relative to the medical instrument fixation portion 70, 84*a*, 84*b*. Once in this position, a first holder section 62, 162 is moved away from a second holder section 64, 164 to a desired position. Once in the desired position, a locking member 74, 174 is rotated to secure the distractor 40, 140 in the desired position such that a desired bone displacement is maintained without further intervention by the surgeon, freeing the surgeon's hands to do other tasks related to the surgical procedure.

To avoid fracturing the medial cortex of the proximal fragment, the wire 92, 192 is inserted sufficiently deeply into the diaphysis. Elevation of the metatarsal head is avoided by ensuring that the distractor 40, 140 remains directly over the medial eminence during displacement. A 1.4 mm diameter k-wire is placed proximate the medial aspect of the first metatarsal and a second k-wire having a 0.9 mm diameter is placed until the tip of the k-wire is positioned proximate to the osteotomy. The osteotomy is then fixed internally with two (2) cannulated screws. Once the lateralization and plantarization are achieved, the k-wires are driven into the metatarsal head. The k-wires are positioned such that the proximal/lateral 1.4 mm k-wire sat in the lateral half of the metatarsal head and the distal/medial 0.9 mm wire sat in the medial half of the metatarsal head. Both the 1.4 mm and 0.9 mm k-wires are placed such that they do not breach the MTP Joint.

What is claimed is:

1. A surgical distractor comprising:
   a first holder section;
   a second holder section coupled to the first holder section using one or more coupling elements coupled to both the first holder section and the second holder section;
   a first displacement element positioned on the first holder section;
   a second displacement element positioned on the second holder section configured to engage the first displacement element;
   a positioning element positioned on the first holder section; and
   a rotatable component having an opening and positioned on the second holder section, wherein
   the rotatable component is configured to rotate around a longitudinal axis along which the rotatable component extends to arrange the opening, and
   the opening extends in a transverse direction with respect to the longitudinal axis.

2. The surgical distractor of claim 1, wherein the one or more coupling elements form a four-bar linkage that is releasably lockable by a releasable fixation screw.

3. The surgical distractor of claim 1, wherein the one or more coupling elements comprises a first bar coupled to the first and second holder sections.

4. The surgical distractor of claim 3, wherein the one or more coupling elements comprises a second bar coupled to the first holder section, the second holder section, and the first bar.

5. The surgical distractor of claim 1, wherein the first displacement element comprises a pawl and the second displacement element comprises a rack with teeth.

6. A surgical distractor comprising:
   a handle;
   one or more coupling elements that form a four-bar linkage actuated by the handle;
   a tissue-engaging element projecting away from and coupled to the four-bar linkage; and
   a rotating component having an opening arranged on a portion of the tissue-engaging element, wherein
   the rotating component is configured to rotate around a longitudinal axis along which the tissue-engaging element projects and the rotating component extends to arrange the opening, and
   the opening extends in a transverse direction with respect to the longitudinal axis.

7. The distractor of claim 6, further comprising a ratchet mechanism configured to maintain a position of the four-bar linkage.

8. The distractor of claim 6, wherein the rotating component further comprises a pin component.

9. The distractor of claim 6, wherein the handle section comprises scissor-style handles.

10. The distractor of claim 6, wherein the handle section comprises plier-style handles.

11. The distractor of claim 6, further comprising a movable member configured to control a position of the tissue-engaging element relative to the rotating component.

12. The distractor of claim 6, further comprising a movable member configured to be moved such that a position of a four-bar linkage is controlled.

13. A distractor comprising:
    a tissue-engaging portion positioned on a first holder section configured to engage a patient's target area;
    a rotatable component having an opening configured to engage a positioning element and positioned on a second holder section;
    a first link positioned on the first holder section; and
    a second link positioned on the second holder section configured to engage the first link; wherein
    the first and second links are configured to engage such that a predetermined distance is maintained between the positioning element and the rotatable component,
    the rotatable component is configured to rotate around a longitudinal axis along which the second holder section and the rotatable component extend to arrange the opening, and
    the opening extends in a transverse direction with respect to the longitudinal axis.

14. A medical distractor comprising:
    a tissue-engaging portion positioned on a first holder section;
    a rotatable component having an opening and positioned on a second holder section;
    a first link positioned on the first holder section; and
    a second link pivotally coupled to the first link and positioned on the second holder section configured to engage the first link; wherein
    first and second displacement elements are configured to engage such that a predetermined distance is maintained between the tissue-engaging portion and the rotatable component,
    the rotatable component is configured to rotate around a longitudinal axis along which the second holder section and the rotatable component extend to arrange the opening, and
    the opening extends in a transverse direction with respect to the longitudinal axis.

* * * * *